United States Patent
Waisman et al.

(10) Patent No.: US 10,197,816 B2
(45) Date of Patent: Feb. 5, 2019

(54) LASER SAFETY GLASSES WITH AN IMPROVED IMAGING SYSTEM

(71) Applicant: LUMENIS LTD., Yokneam Ilit (IL)

(72) Inventors: Tal Waisman, Haifa (IL); Moshe Elazar, Kadima-Tzoran (IL); Ofer Chobotaru, Afula (IL); Assaf Preiss, Shimshit (IL)

(73) Assignee: LUMENIS LTD., Yokneam (IL)

( * ) Notice: Subject to any disclaimer, the term of this patent is extended or adjusted under 35 U.S.C. 154(b) by 0 days.

(21) Appl. No.: 15/163,847

(22) Filed: May 25, 2016

(65) Prior Publication Data

US 2016/0349539 A1    Dec. 1, 2016

Related U.S. Application Data

(60) Provisional application No. 62/166,188, filed on May 26, 2015.

(51) Int. Cl.
*G06F 3/01* (2006.01)
*G02C 11/00* (2006.01)
*A61F 9/02* (2006.01)
*G02C 7/10* (2006.01)
*G02B 27/01* (2006.01)
*G02B 5/22* (2006.01)

(52) U.S. Cl.
CPC ............. *G02C 11/10* (2013.01); *A61F 9/022* (2013.01); *G02B 5/22* (2013.01); *G02B 27/0172* (2013.01); *G02C 7/10* (2013.01); *G06F 3/017* (2013.01); *G02B 2027/0178* (2013.01); *G02B 2027/0187* (2013.01)

(58) Field of Classification Search
CPC .......... G06F 3/017; A61F 9/022; G02B 5/22; G02B 27/0172; G02B 2027/0178; G02C 7/10
USPC ............................................ 345/7–9; 607/88
See application file for complete search history.

(56) References Cited

U.S. PATENT DOCUMENTS

| | | | |
|---|---|---|---|
| 5,146,623 A * | 9/1992 | Paysan ...................... | A61F 9/02 2/12 |
| 8,203,502 B1 * | 6/2012 | Chi ....................... | G02B 27/017 345/7 |
| 9,551,872 B1 * | 1/2017 | Kress .................. | G02B 27/0172 |
| 2005/0206583 A1 * | 9/2005 | Lemelson .......... | A61B 1/00048 345/7 |

* cited by examiner

*Primary Examiner* — Michael Pervan
(74) *Attorney, Agent, or Firm* — ISUS Intellectual Property PLL

(57) ABSTRACT

Laser safety glasses for use in laser medical and cosmetic procedures on a patient include a pair of safety glasses wherein the safety glasses include a pair of lenses, one or more of the lenses being structured to absorb one or more predetermined wavelengths of laser energy light; a screen is mounted on at least one lens of the pair of lenses, the screen being operatively associated with a system one of internal or external to the glasses configured to generate and provide information regarding the medical or cosmetic procedure to a wearer of the laser safety glasses through the screen.

3 Claims, 3 Drawing Sheets

LASER SAFETY GLASSES WITH AN IMPROVED IMAGING SYSTEM

RELATED APPLICATIONS

This application is related to and claims priority to U.S. Provisional Application Ser. No. 62/166,188, filed May 26, 2015, the entirety of which disclosure is herein incorporated by reference.

BACKGROUND OF THE PRESENT INVENTION

In recent years there is a growing presence of lasers in operating rooms and points of care. The proliferation of laser technologies into the medical field is driven by a wide diversity of better and cheaper laser generators and delivery systems. The availability and reliability of these technologies further expose more researchers and practitioners to their potential contribution in medicine and more laser applications are developed.

Laser light may cause eye injuries and therefore safety measures are involved with laser applications. Laser tissue interaction is a function, among other things, of the laser wavelength. Thermal damage is the predominant cause of laser radiation injury. However, photochemical or shock waves associated with cavitation may also injure the eye tissue. Light visible to near infrared wavelengths can penetrate the cornea and the lens of the eye and may damage the retina. A transient increase of 10° C. may destroy retinal photoreceptors.

Photochemical reaction in the retina may be triggered by exposure to blue or ultra violet light. Light shorter than 400 nm is mainly absorbed by the eye lens while light shorter than 300 nm is mainly absorbed by the cornea. Near infrared light causes mainly thermal damage to inner organs of the eye while longer wavelengths risks injury to more frontal parts of the eye e.g. lens and cornea. Since infrared light does not trigger the blink reflex, the risk is higher than with visible light. Maximum permissible exposure is regulated by different governmental and non-governmental bodies and laser are classified based on the notion of accessible emission limits defined for each class. Most of the medical lasers are classified as class 4.

An existing body of laws and regulations require eye protection for people that are operating or may be exposed to lasers of classes 3B and 4. Protective eyewear should be worn such as spectacles or goggles with an appropriate filtering capabilities. Again, for different wavelengths of laser different filters are required to absorb reflected or scattered light. For example, eyewear absorbing 532 nm typically has an orange appearance transmitting wavelengths higher than 550 nm. Such eyewear will provide no protection for laser radiation with longer wavelength than 550 nm e.g. 800 nm.

Some lasers may emit more than a single wavelength and protection from such lasers may be required to have multiple range protection. The optical density of the protective lens, which defines the ability of such lens to attenuate the beam power is also a key factor in defining the appropriate protection to a specific laser.

U.S. Pat. No. 5,146,623 discloses safety spectacles which are protective against laser radiation having a frame structure which further avoids any light reaching the eyes from the side. German patent no. DE 2347019 discloses a safety filter for protecting the eyes against multi-wavelength laser beams and comprises two glass layers each filters different wavelength.

Also disclosed in the prior art are magnifying surgical spectacles such as in U.S. Pat. No. 3,592,525 having a head piece for illuminating target tissue and secondary magnifying pair of lenses. Magnifying binocular glasses having integral CCD for capturing and transmitting images of a surgical site are disclosed in JP patent application no. JS2003204972.

Advanced and smaller display technology, lasers and scanners have led to the proliferation of head mounted displays. U.S. Pat. No. 5,914,770 discloses ophthalmological examination comprises spectacles capable to generate a reflecting image projected directly onto the wearer's eye. Such a system is configured to combine the real time image observed by the physician with an external data projected on real time onto such image.

Augmented reality, enhancing the user's perception of and interaction with the real world through supplementing the real world with virtual objects that appear to coexist in the same space as the real world has become more and more available with recent developments of enabling technologies in different fields. Among these fields is the medical field. Such enabling technologies include see-through displays which enable the projection of an image into the field of view of an observer or projection displays allowing the projection of an image on physical objects in the real world that are to be augmented.

The medical field augmented reality and visualization systems may combine a real time image with an image which is rendered based on datasets collected from MRI, CT or an Ultrasound image in order to produce an augmented picture in the field of view of the physician. One such laser projection augmented reality system for computer assisted surgery is disclosed for example by Neil D. Glossop and Zhanhe Wang. Augmented reality imaging apparatus is disclosed in U.S. Pat. No. 8,872,941, U.S. Pat. No. 6,937,400 or in WO14014145.

U.S. Pat. No. 8,203,502 further discloses a system and method for interfacing with a wearable heads-up display with a finger operable input device. The '502 patent further discloses projecting virtual controlling elements in the field of view of a user who can then interact with these controllers by figure gestures.

It is one aspect of the present invention to combine an augmented reality system with laser safety spectacles to enable a better way to control a surgical laser.

SUMMARY OF THE PRESENT INVENTION

In an aspect, laser safety glasses for use in laser medical and cosmetic procedures on a patient include a pair of safety glasses wherein the safety glasses include a pair of lenses, one or more of the lenses being structured to absorb one or more predetermined wavelengths of laser energy light; a screen mounted on at least one lens of the pair of lenses, the screen being operatively associated with a system one of internal or external to the glasses configured to generate and provide one or more images containing information regarding the medical or cosmetic procedure to a wearer of the laser safety glasses through the screen. The screen may be constructed as a see-through screen.

In another aspect, the information the system generates and provides to the wearer may include one of more parameters of: energy level of system, pulse width of a laser energy source operatively connected to the system, graphical or textual information related to the patient, images of the medical or cosmetic site, the position of a aiming laser beam, instructions for the procedure, patient body vital information or status of the laser as being on or off.

In a further aspect, a sending unit may be operatively associated with the glasses to project one or more images of information onto the screen. The sending unit might be connected in one of wired or wireless is to a programmed controller of the system. A virtual controller allows the wearer to control specified parameters of the system generated on the screen by one or more of movement or position of one or more body organ such as a finger, hand, foot, eye lid, pupil or other.

In yet a further aspect, one or more sensors mounted on the glasses detect the one or more of movement or position of the one or more fingers on the wearer's hands. The detection of one or more of movement or position by the one or more sensors causes the virtual controller to control said certain parameters.

In another aspect, the laser safety glasses further may include a foot switch to activate a laser device operatively associated with the system. The activation of the laser device requires both pushing of the foot switch and activation of the virtual controller. A control unit allows the wearer to interact with the information provided to the wearer through the screen. The control unit may be one of a: mouse device, a ball roller mouse or a stick controller.

In yet a further aspect, laser safety glasses for use in laser medical and cosmetic procedures on a patient includes a pair of safety glasses wherein the safety glasses include a pair of lenses; a projector operatively connected to the safety glasses to project light containing one or more wavelengths of light onto the pair of lenses. The one or more projected wavelengths may be one or more wavelengths to absorb one or more predetermined wavelengths of laser energy light. The projector projects light one of on the back surface of the pair of lenses or the front surface of the pair of lenses.

In another aspect, a laser light producing system is connected to the glasses and is configured to control the one or more wavelengths of light projected onto the pair of lenses by matching the one or more wavelengths of projected light to the one or more wavelengths of laser light energy produced by the system. The one or more wavelengths of projected light are user selectable.

BRIEF DESCRIPTION OF THE DRAWING FIGURES

DETAILED DESCRIPTION OF THE PRESENT INVENTION

Figure 1:
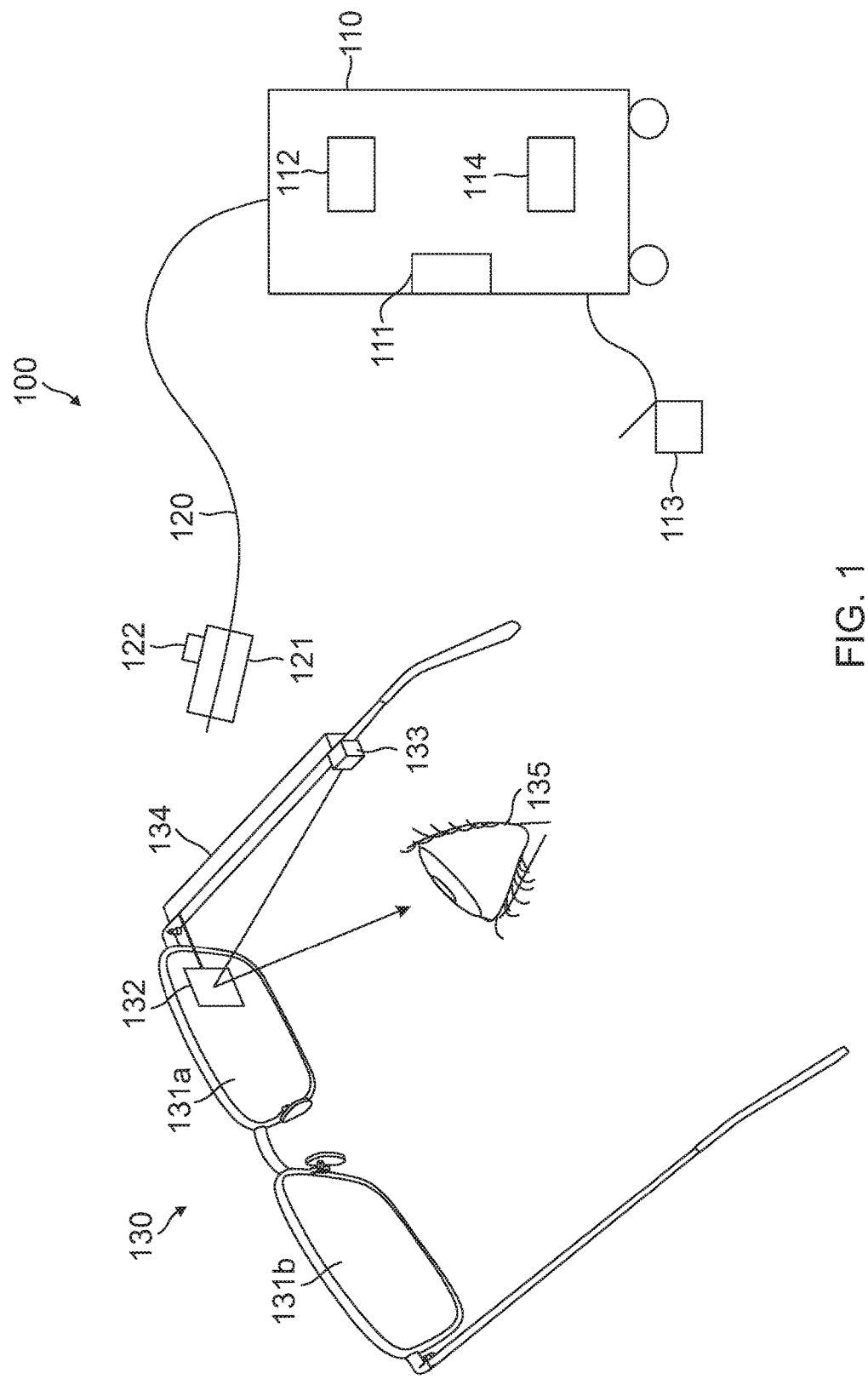
FIG. 1 illustrates a laser system incorporating the imaging safety glasses of the present invention.

According to one aspect of the invention there is provided laser safety glasses which include enhanced imaging capabilities. Referring to FIG. 1, a laser system 100 is shown. Laser system 100 comprises a laser system 110 having laser delivery system 120. Laser system 110 may be for example a solid state laser such as for example NdYAG, Holmium, or Erbium. Alternatively, such a laser system may be, for example, a gas-fired laser such as a CO2, a diode laser, Alexandrite, Ruby or a fiber laser. In addition, laser system 110 may be configured to generate more than one wavelength. Laser delivery systems may include, for example, an optical fiber, a wave guide or an articulated arm.

Laser system 100 further includes glasses or goggles 130 having lenses 131a and 131b which are configured to protect the operator's eye 135 by filtering laser wavelength or wavelengths generated by laser system 110 and transmitted by or through delivery system 120 onto a surgical site. At least one lens 131a or 131b of glasses 130 may further include a see-through screen 132. See-through screen 132 is connected to a sending unit 133 through connecting unit 134 and is located in the field of view of operator's eye 135. Sending unit 133, which may be a known programmed or programmable controller, is configured to connect with wires or wirelessly with transmitting—receiving unit 111 in laser system 110. Laser controller 112, through unit 111, sends information to sending unit 133 to be displayed in screen 132. It should be mentioned that according to this aspect of the invention 132 may also include a reflective area and sending unit 133 may be configured to project an image on reflecting area 132 located in the field of view of the operator's eye 135.

Figure 2:
FIGS. 2a and 2b illustrate virtual controllers for use with the glasses of FIG. 1

Referring now to FIG. 2a, a virtual controller of the laser is shown. According to this aspect of the invention, an image projected on or rendered in element 132 may include virtual controls which may control the working parameters of laser system 110. Shown in FIG. 2a is an example of a virtual controller which may control the energy level of the system. In this example, virtual controller 21 is configured to raise the energy level generated by the laser system 110 while virtual controller 22 is configured to lower such energy. Another example of a virtual controller is shown in FIG. 2b in which the ability to increase or decrease the laser pulse width is shown. According to this aspect of the invention, any other parameter which can be controlled by an operator through a regular user interface 114 of laser system 110 may also be converted into a virtual controller which can further be presented in the field of view of the laser operator who wears glasses 130.

Figure 3:
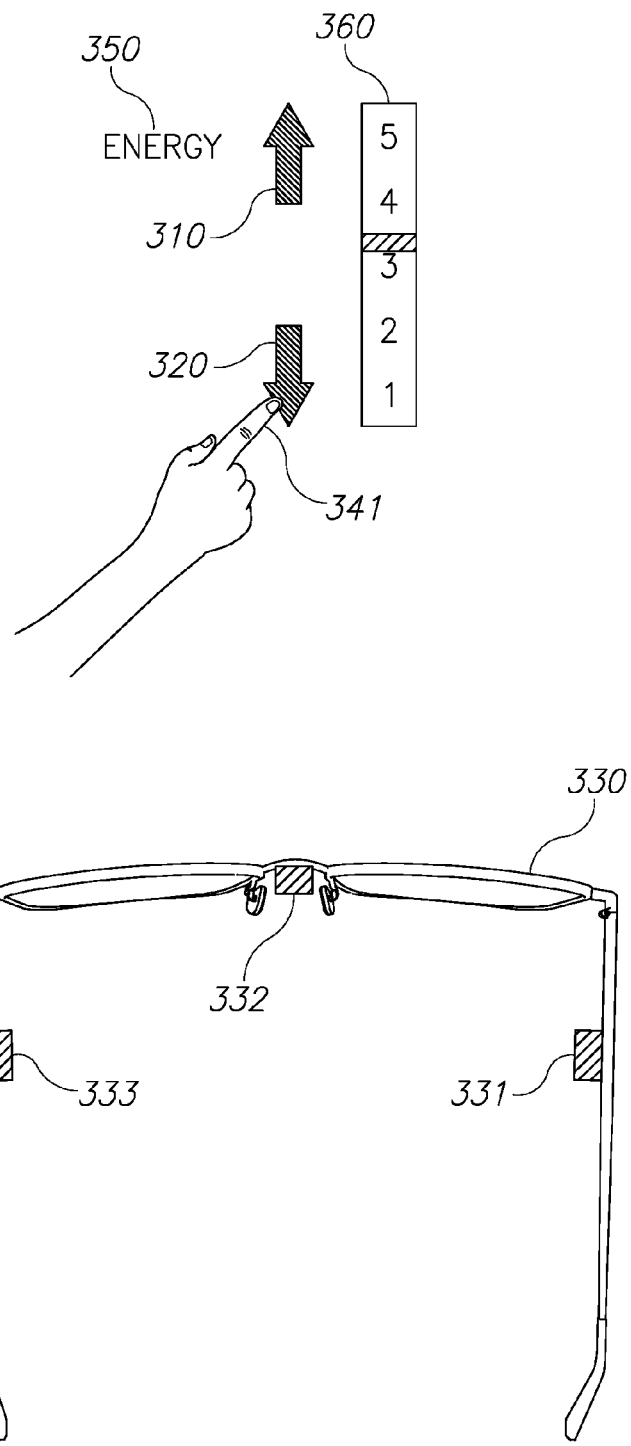
FIG. 3 illustrates another embodiment of virtual controllers for use with the glasses of FIG. 1.

Referring now to FIG. 3, laser safety glasses 330 are shown together with two examples of virtual controllers 310 and 320. An operator operating a laser system according to this invention and wearing glasses 330 will see such virtual controllers 310 and 320 together with their associated text elements 350 and graphical elements 360 in the field of view. Further, according to this aspect of the invention, the operator may use his/her body organ such as a finger, hand, foot, eye lid, pupil or other 341 to interact with virtual controllers such as 310 or 320. Sensor elements 331, 332 or 333 are configured to detect and analyze the position of fingertip 341 and/or its movement in order to interpret the way an operator interacts with the virtual controllers and send these commands to laser controller 112. For example, tapping with fingertip 341 on the tip of arrow 320 may be identified as a command by the operator, for example, to reduce the level of energy to be produced by laser system 110.

One virtual controller among many others, may be for example, a controller to turn on the laser. Medical lasers in the prior art are usually operated by a foot switch. A foot switch 113 is shown in FIG. 1. As mentioned above, one of the virtual controllers may be the controller to turn on the laser. According to one embodiment of the present invention, laser system 110 may have safety loop so that a virtual controller may turn on the laser only if the foot switch is pressed. According to another embodiment of the invention, a virtual controller may turn on the laser even if the footswitch is not pressed.

Laser delivery systems, like that shown at 120 may be configured to be incorporated in another surgical instrument such as an endoscope, a laparoscope or for example a ureter scope. Such a surgical element is shown in FIG. 1 as element 121. During the surgery, a laser operator who wears safety glasses 130 according this invention will be busy with his hands most of the time managing and manipulating element 121 or different instruments which may also be introduced into the surgical site through element 121. Such instruments may be for example a morcellator, a suction port, an irrigating port or a visualization unit. According to another embodiment of the present invention, a control unit 122, such as a computer mouse or other similar control device, is configured to be positioned adjacent to element 121 where the operator's hands are located most of the time.

Such control unit 122 is configured to interact with a cursor shown in the field of view of an operator's eye 135 to allow a more intuitive interaction with virtual controllers as described above. Control 122 may be a stand-alone unit which is configured to be placed on instrument 121 or it can be an integral part of element 121. Control unit 122 may include for example a ball mouse or a stick mouse to control the movement of the cursor in the field of view of the operator by rolling a ball or by pushing stick. In addition, control 122 may further include a selecting mechanism such as a button as known to the skilled man in the art to initiate an interaction between the cursor and the virtual controllers. Control unit 122 may also be implemented in other ways, for example as an arrangement of dedicated pushbuttons which may be read and interpreted by controller 111.

According to another aspect of the invention, as mentioned above, there is provided a pair of laser safety glasses with a pair of lenses which are configured to filter at least one wavelength or at least one wavelength spectrum/range or combination of spectrums/ranges. Laser safety lenses are known to those skilled in the art and are commercially available from companies such as for example, Laser Safety Industries. Lenses which are configured to attenuate specific wavelengths or combination of wavelengths tend to be of a specific typical color and lose some of their transparency.

For example, Polycarbonate lenses which are configured to attenuate far IR wavelength such as for example Holmium, Erbium or CO2 tend to have some grayish color. Glass lenses which filter and attenuate both UV and IR wavelengths tend to get an orange color while safety glasses which attenuate mainly 190-450 nm tend to become yellow, lenses which filter mainly 680-700 nm tend to become blueish, lenses which filter mainly 820-1720 or about 755 nm tend to become green and lenses which filter mainly 715-810 tend to be purple. The color of the lens indicates which color the lens best reflects.

Therefore, according to this aspect of the invention, there is provided a laser safety glasses with an integral projection system which is configured to project an image on an inner side of at least one lens facing an operator's eye to provide an image which is best reflected from the specific lens in use, in order to provide a high quality image with good intensity. For example, a safety lens which tends to have a green color, will best reflect a green color light. Therefore, according to this aspect of the invention, the projection system of the present invention will be configured to project green light on the internal surface of a green laser safety lens which is facing an operator's eye in order to create a good quality image.

With laser safety lenses which have different colors, according to this aspect of the invention, an appropriate image projecting system may be chosen such that the reflection from such lens will be maximized and therefore the intensity of the image will be maximized. One of the advantages of using the reflectance properties of the laser safety lens to reflect the image projected onto the lens and configured to be seen by the laser operator is that no dedicated see through screen or special coating required in order to generate a reflected image.

Thus, the present invention may provide user safety glasses for use in laser medical and cosmetic procedures on a patient including a pair of safety glasses wherein the safety glasses include a pair of lenses; a projector may be provided which is operatively connected to the safety glasses and projects light containing one or more wavelengths of light onto the pair of lenses. The one or more projected wavelengths may be selected to be the one or more wavelengths that absorb one or more predetermined wavelengths of laser energy light from a laser light energy producing system. The laser light producing system may connected to the glasses and be configured to control the one or more wavelengths of light projected onto the pair of lenses by matching, through the use of a programmable controller, the one or more wavelengths of projected light to the one or more wavelengths of laser light energy produced by the system.

In a simpler embodiment, the one or more wavelengths of light projected onto the pair of lenses may be selectable. Such projected light may be projected onto either the back or the front surface of the lenses.

According to another aspect of the invention, other graphical or textual information related to the patient, the target tissue in a surgical site or information related to the condition or state of a laser delivery system or a laser operating beam or a laser aiming beam may be displayed in the field of view of the laser operator. The following are few non-limiting examples. An image acquired from a visualization system of the target tissue in a surgical site may be projected or rendered in the field of view of the eyewear subject to at least one aspect of the invention. As another example, the distance between the distal-end of the laser delivery system such as an optical fiber, to the target tissue such as a urinary stone, may be displayed and marked in the eyewear according to some aspects of the invention.

According to another example, the integrity of the laser delivery system, the optical coupling with the main laser console may also be indicated visually or graphically in the field of view of the laser operator using the eyewear according to this invention. Images acquired before or during a surgery of the target tissue by other systems such as for example, CT, MRI or Ultrasound may also be generated in the field of view of a laser operator. The position or the orientation of the surgical laser beam or the aiming laser beam of the surgical system may be registered and shown on any such acquired images. A registered image may also allow the registration of the existing location of the aiming laser beam, the orientation of the laser delivery system, so that the laser operator may get a real time indication of such parameters in the field of view.

What we claim is:
1. Laser safety glasses for use in laser medical and cosmetic procedures on a patient comprising:
   a pair of safety glasses wherein the safety glasses include
     a pair of lenses;
   each lens is characterized by reflecting one or more
     wavelengths and therefore is characterized by having a first color and is configured to absorb one or more wavelengths having a second color;
a projector operatively connected to the safety glasses to project light containing one or more wavelengths of light onto the pair of lenses;
the one or more projected wavelengths being one or more wavelengths characterizing the first color so that the reflection of the projected light from the internal surface of the at least one lens is maximized; and
wherein a laser light producing system is connected to the glasses and is configured to control the projector having one or more wavelengths of light and to project laser light which is not filtered by the lenses in the glasses.

2. The laser safety glasses of claim 1, wherein the projector projects light one of on the back surface of the pair of lenses or the front surface of the pair of lenses.

3. The laser safety glasses of claim 1, wherein the one or more wavelengths of projected light are user selectable.

* * * * *